(12) United States Patent
Mault

(10) Patent No.: US 6,309,360 B1
(45) Date of Patent: Oct. 30, 2001

(54) RESPIRATORY CALORIMETER

(76) Inventor: James R. Mault, 1580 Blakcomb Ct., Evergreen, CO (US) 80439

(*) Notice: Subject to any disclaimer, the term of this patent is extended or adjusted under 35 U.S.C. 154(b) by 0 days.

(21) Appl. No.: 09/008,435

(22) Filed: Jan. 16, 1998

Related U.S. Application Data

(60) Provisional application No. 60/042,079, filed on Mar. 28, 1997, and provisional application No. 60/041,594, filed on Mar. 17, 1997.

(51) Int. Cl.[7] ..................................................... A61N 5/00
(52) U.S. Cl. ...................... 600/531; 600/529; 128/200.24
(58) Field of Search .................................... 600/529–538; 128/200.24

(56) References Cited

U.S. PATENT DOCUMENTS

| 2,630,798 | 3/1953 | White et al. ........................ 128/2.07 |
| 2,826,912 | 3/1958 | Kritz . |
| 2,831,348 | 4/1958 | Kritz . |
| 2,838,399 | 6/1958 | Vogel, Jr. ................................ 99/48 |
| 2,869,357 | 11/1959 | Kritz . |
| 2,911,825 | 11/1959 | Kritz . |
| 2,920,012 | 1/1960 | Sanders et al. ..................... 167/51.5 |
| 3,213,684 | 10/1965 | Seaton et al. .......................... 73/190 |
| 3,220,255 | 11/1965 | Scranton et al. . |
| 3,250,270 | 5/1966 | Bloom ................................ 128/2.07 |
| 3,306,283 | 2/1967 | Arp ..................................... 128/2.07 |
| 3,523,529 | 8/1970 | Kissen ................................ 128/2.07 |
| 3,527,205 | 9/1970 | Jones ................................. 128/2.08 |
| 3,681,197 | 8/1972 | Smith .................................... 195/63 |

(List continued on next page.)

FOREIGN PATENT DOCUMENTS

| 198 10 476 | 9/1998 | (DE) . |
| 0459647A2 | 10/1991 | (EP) . |
| 0 712 638 | 12/1995 | (EP) . |
| 2323292 | 9/1998 | (GB) . |
| WO 96/40340 | 12/1996 | (WO) . |

OTHER PUBLICATIONS

Medical Progress Through Technology, vol. 9, No. 1, 1982, Berlin (D) pp. 27–32, R. Salminen et al. "Computerized Breath–by–Breath Analysis of Respiratory Variables During Exercise".

British Journal of Anaesthesia, vol. 49, 1977, London (GB) pp. 575–587, J.A. Bushman et al. "Closed Circuit Anaesthesia".

IEEE Transactions on Biomedical Engineering, vol. 35, No. 9, Sep. 1988, pp. 653–659, Capek et al., "Noninvasive Measurement of Cardiac Output Using Partial $CO_2$ Rebreathing".

Clinics in Chest Medicine [Review], vol. 10, 1989, pp. 255–264, Heigenhauser et al., "Measurement of Cardiac Output by Carbon Dioxide Rebreathing Methods".

*Primary Examiner*—Max Hindenburg
*Assistant Examiner*—Michael Astorino
(74) *Attorney, Agent, or Firm*—Gifford, Krass, Groh, Sprinkle, Anderson & Citkowski, P.C.

(57) ABSTRACT

An indirect calorimeter for measuring the subject's oxygen consumption per unit time employs a mouthpiece through which the subject breathes for a period of time. Conduits connect the mouthpiece to a flow meter and a capnometer so that the subject's inhalations and exhalations pass through the flow meter and the exhalations also pass through the capnometer. Electrical signals from the flow meter and capnometer are provided to a computer which calculates the $CO_2$ exhaled by the subject during the test by integrating the instantaneous $CO_2$ content of an exhalation as measured by the capnometer over the volume as measured by the flow meter and subtracts that quantity from the exhaled volume and subtracts their difference from the inhaled volume.

In alternative embodiments the system can also measure the subject's Cardiac Output and Delivered Oxygen.

18 Claims, 2 Drawing Sheets

U.S. PATENT DOCUMENTS

| | | | |
|---|---|---|---|
| 3,726,270 | 4/1973 | Griffis et al. | 128/2.08 |
| 3,797,480 | 3/1974 | Williams | 128/2.08 |
| 3,799,149 | 3/1974 | Rummel et al. | 128/2.07 |
| 3,814,091 | 6/1974 | Henkin | 128/188 |
| 3,834,375 | 9/1974 | Sanctuary et al. | 128/2.07 |
| 3,895,630 | 7/1975 | Bachman | 128/2.07 |
| 3,938,551 | 2/1976 | Henkin | 137/613 |
| 3,962,917 | 6/1976 | Terada . | |
| 4,003,396 | 1/1977 | Fleischmann | 137/83 |
| 4,051,847 | 10/1977 | Henkin | 128/145.6 |
| 4,078,554 | 3/1978 | Lemaitre et al. . | |
| 4,186,735 | 2/1980 | Henneman et al. | 128/201.25 |
| 4,188,946 | 2/1980 | Watson et al. | 128/204.22 |
| 4,197,857 | 4/1980 | Osborn . | |
| 4,200,094 | 4/1980 | Gedeon et al. | 128/201.13 |
| 4,211,239 | 7/1980 | Raemer et al. | 128/716 |
| 4,221,224 | 9/1980 | Clark | 128/718 |
| 4,230,108 | 10/1980 | Young . | |
| 4,341,867 | 7/1982 | Johansen | 435/189 |
| 4,359,057 | 11/1982 | Manzella | 128/718 |
| 4,368,740 | 1/1983 | Binder | 128/718 |
| 4,386,604 | 6/1983 | Hershey | 128/718 |
| 4,425,805 | 1/1984 | Ogura et al. . | |
| 4,440,177 | 4/1984 | Anderson et al. . | |
| 4,444,201 | 4/1984 | Itoh | 128/716 |
| 4,463,764 | 8/1984 | Anderson et al. . | |
| 4,572,208 | 2/1986 | Cutler et al. | 128/718 |
| 4,598,700 | 7/1986 | Tamm | 128/671 |
| 4,608,995 | 9/1986 | Linnarsson et al. | 128/713 |
| 4,619,269 | 10/1986 | Cutler et al. | 128/719 |
| 4,648,396 | 3/1987 | Raemer . | |
| 4,658,832 | 4/1987 | Brugnoli . | |
| 4,753,245 | 6/1988 | Gedeon | 128/718 |
| 4,756,670 | 7/1988 | Arai | 417/43 |
| 4,781,184 | 11/1988 | Fife | 128/205.12 |
| 4,796,639 | 1/1989 | Snow et al. . | |
| 4,850,371 | 7/1989 | Broadhurst et al. . | |
| 4,856,531 | 8/1989 | Merilainen . | |
| 4,909,259 | 3/1990 | Tehrani . | |
| 4,914,959 | 4/1990 | Mylvaganam et al. . | |
| 4,917,108 | 4/1990 | Mault . | |
| 4,955,946 | 9/1990 | Mount et al. . | |
| 4,986,268 | 1/1991 | Tehrani . | |
| 4,998,018 | 3/1991 | Kurahashi et al. . | |
| 5,022,406 | 6/1991 | Tomlinson | 128/719 |
| 5,038,773 | 8/1991 | Norlien et al. . | |
| 5,038,792 | 8/1991 | Mault | 128/718 |
| 5,042,500 | 8/1991 | Norlien et al. . | |
| 5,042,501 | 8/1991 | Kenny et al. . | |
| 5,060,506 | 10/1991 | Douglas . | |
| 5,060,655 | 10/1991 | Rudolph . | |
| 5,060,656 | 10/1991 | Howard | 128/718 |
| 5,069,220 | 12/1991 | Casparie et al. | 128/719 |
| 5,072,737 | 12/1991 | Goulding | 128/718 |
| 5,081,871 | 1/1992 | Glaser . | |
| 5,095,900 | 3/1992 | Fertig et al. . | |
| 5,095,913 | 3/1992 | Yelderman et al. | 128/719 |
| 5,117,674 | 6/1992 | Howard . | |
| 5,119,825 | 6/1992 | Huhn . | |
| 5,178,155 | * 1/1993 | Mault | 600/531 |
| 5,179,958 | * 1/1993 | Mault | 600/531 |
| 5,214,966 | 6/1993 | Delsing . | |
| 5,233,996 | 8/1993 | Coleman et al. . | |
| 5,282,473 | 2/1994 | Braig et al. . | |
| 5,285,794 | 2/1994 | Lynch | 128/719 |
| 5,293,875 | 3/1994 | Stone | 128/719 |
| 5,299,579 | 4/1994 | Gedeon et al. . | |
| 5,303,712 | 4/1994 | Van Duren . | |
| 5,309,921 | 5/1994 | Kisner et al. . | |
| 5,326,973 | 7/1994 | Eckerbom et al. . | |
| 5,355,879 | 10/1994 | Brain . | |
| 5,357,972 | 10/1994 | Norlein . | |
| 5,363,857 | 11/1994 | Howard . | |
| 5,398,695 | 3/1995 | Anderson et al. . | |
| 5,402,796 | 4/1995 | Packer et al. | 128/719 |
| 5,419,326 | 5/1995 | Harnoncourt . | |
| 5,425,374 | 6/1995 | Ueda et al. . | |
| 5,450,193 | 9/1995 | Carlsen et al. . | |
| 5,468,961 | * 11/1995 | Gradon et al. | 250/345 |
| 5,503,151 | 4/1996 | Harnoncourt et al. . | |
| 5,570,697 | 11/1996 | Walker et al. | 128/719 |
| 5,632,281 | * 5/1997 | Rayburn | 600/532 |
| 5,645,071 | 7/1997 | Harnoncourt et al. | 128/719 |
| 5,647,370 | 7/1997 | Harnoncourt . | |
| 5,676,132 | 10/1997 | Tillotson et al. . | |
| 5,705,735 | * 1/1998 | Acorn | 128/204.23 |
| 5,754,288 | 5/1998 | Yamamoto et al. . | |
| 5,789,660 | * 8/1998 | Kofoed et al. | 73/23.3 |
| 5,796,009 | 8/1998 | Delsing . | |
| 5,800,360 | 9/1998 | Kisner et al. . | |
| 5,816,246 | 10/1998 | Mirza . | |
| 5,831,175 | 11/1998 | Fletcher-Haynes . | |
| 5,834,626 | 11/1998 | DeCastro et al. . | |
| 5,836,300 | * 11/1998 | Mault | 600/532 |
| 5,922,610 | 7/1999 | Alving et al. . | |
| 5,932,812 | 8/1999 | Delsing . | |
| 5,957,858 | 9/1999 | Micheels et al. . | |
| 6,010,459 | 1/2000 | Silkoff et al. . | |
| 6,044,843 | 4/2000 | O'Neil et al. . | |

\* cited by examiner

RESPIRATORY CALORIMETER

RELATED APPLICATIONS

This application claims the benefit of Provisional Patent Application Ser. Nos. 60/041,594 and 60/042,079, filed Mar. 17, 1997 and Mar. 28, 1997, respectively.

FIELD OF THE INVENTION

This invention relates to indirect calorimeters for determining the metabolic rates of subjects by measuring their oxygen consumption during respiration over a period of time, and more particularly to such a calorimeter employing a flow meter and a capnometer to compute the difference between the inhaled gas volume and the volume of the exhaled gas less the exhaled $CO_2$ volume.

BACKGROUND OF THE INVENTION

Measurement of the energy expenditure of humans is important for a number of reasons, including the determination of the proper caloric content for feedings of hospitalized patients whose metabolisms may deviate from normal values, the monitoring of progress of weight loss diets to allow the adjustment of caloric inputs to achieve a target loss and the determination of energy expenditure during exercise.

A variety of indirect calorimeters for measuring oxygen consumption during respiration have been devised. One form of respiratory calorimeter, disclosed in my U.S. Pat. Nos. 4,917,108; 5,038,792; 5,179,985 and 5,178,155, measures the volume of a subject's inhalations over a period of time, and the volume of the subject's exhalations after carbon dioxide in the exhalations has been removed by an absorbent scrubber. These measurements are integrated over the time of measurement and the difference between the two summed volumes is a measure of the subject's oxygen consumption. This follows from the fact that inhaled oxygen is either absorbed into the blood in the subject's lungs or expelled during exhalation. Some portion of the blood absorbed oxygen is replaced with $CO_2$. When the $CO_2$ is removed from the exhaled volume, the summed difference between inhalation and exhalation volume over a period of time is equal to the absorbed oxygen.

In some versions of these prior calorimeters a capnometer was also used to measure the instantaneous value of the exhaled $CO_2$ in a breath allowing the calculation of $CO_2$ production, Resting Energy Expenditure (REE) and Respiratory Quotient (RQ).

The absorbent scrubber used with these previous systems, such as sodium hydroxide or calcium hydroxide, which reacts with the $CO_2$ to form water plus a salt, has a limited ability to absorb $CO_2$ and must be replenished after a period of use. The scrubber is also large and heavy relative to the other components of the calorimeter.

SUMMARY OF THE PRESENT INVENTION

The present invention eliminates the need for the carbon dioxide scrubber used in my previous devices by measuring the volume of exhaled carbon dioxide and subtracting that volume from the total exhaled volume over the measurement period to calculate a sum which is then subtracted from the inhaled volume to arrive at $VO_2$. The volume of exhaled carbon dioxide is preferably measured by integrating the instantaneous carbon dioxide percentage of the exhalation, as measured by a capnometer, over the exhaled volume as measured by a flow meter: $VCO_2 = V_e(\% \ CO_2)$.

The flow meter generates an electrical signal as a function of the instantaneous flow volume and this signal is preferably sent to microprocessor-based computer along with the electrical output of a capnometer sensor. A preferred embodiment of the invention uses a bidirectional flow meter to measure both the inhaled and exhaled flow volume. A temperature and/or humidity conditioner may be utilized to equalize the temperature and/or humidity of the incoming air to that of the exhaled air so that uniform flow measurements may be made. Alternatively, the system could receive signals representing temperature, humidity and/or barometric pressure from sensors disposed in the calorimeter or externally, or keyboard entries and calculate correction factors for the flow measurement based on the signals. In this configuration the distinction between inhalations and exhalations is determined by the presence or absence of $CO_2$ in the flowing gas is measured by the capnometer or by a zero crossing algorithm applied to the output of the flow meter.

Alternatively, the invention might employ a unidirectional flow sensor and conduits and one-way valves arranged so that both the inhaled flow volume and the exhaled flow volume pass through the flow meter in the same direction possibly providing a more precise flow measurement than the bidirectional flow sensor of the preferred embodiment.

The microprocessor, in addition to calculating and displaying the $VO_2$, may calculate and display REE, RQ and the rate of carbon dioxide production.

Another alternative embodiment of my invention may be used to calculate the subject's Cardiac Output implementing the noninvasive method of cardiac output measurement using partial $CO_2$ rebreathing described in an article by Capek and Roy in *IEEE Transactions and Biomedical Engineering*, Vol. 35, pages 653–61, 1988. This embodiment of the invention employs a two stage measurement. In the first stage, the device is configured in essentially the same manner as the other embodiments of the invention to measure oxygen consumption. Over a period of use, such as three minutes, the microprocessor measures $VO_2$, $VCO_2$, and the end-tidal $CO_2$ ($etCO_2$) which is the carbon dioxide content of a breath at the end of an exhalation. These values are stored and the device is then switched to a configuration in which the end portion of each exhalation is not expelled from the device but is rather captured so that it forms the initial portion of the gas provided to the subject during the next inhalation. This is achieved by creating a dead space chamber in the exhalation passage. The subject breaths in this manner for a short period such as 30 seconds. During this period the breath-to-breath $etCO_2$ and the total $VCO_2$ are recorded. The computer then implements the calculation:

$$C.O. = \frac{\Delta VCO_2}{\Delta etCO_2}$$

where $\Delta VCO_2$ equals the difference in the total volume of exhaled $CO_2$, per breath, during the two recordings and $\Delta etCO_2$ is the difference in the end-tidal $CO_2$ between the two recordings.

BRIEF DESCRIPTION OF THE DRAWINGS

Other advantages and applications of the present invention will be made apparent by the following detailed description of several embodiments of the invention. The description makes reference to the accompanying drawings in which.

DETAILED DESCRIPTION OF THE INVENTION

Figure 1:
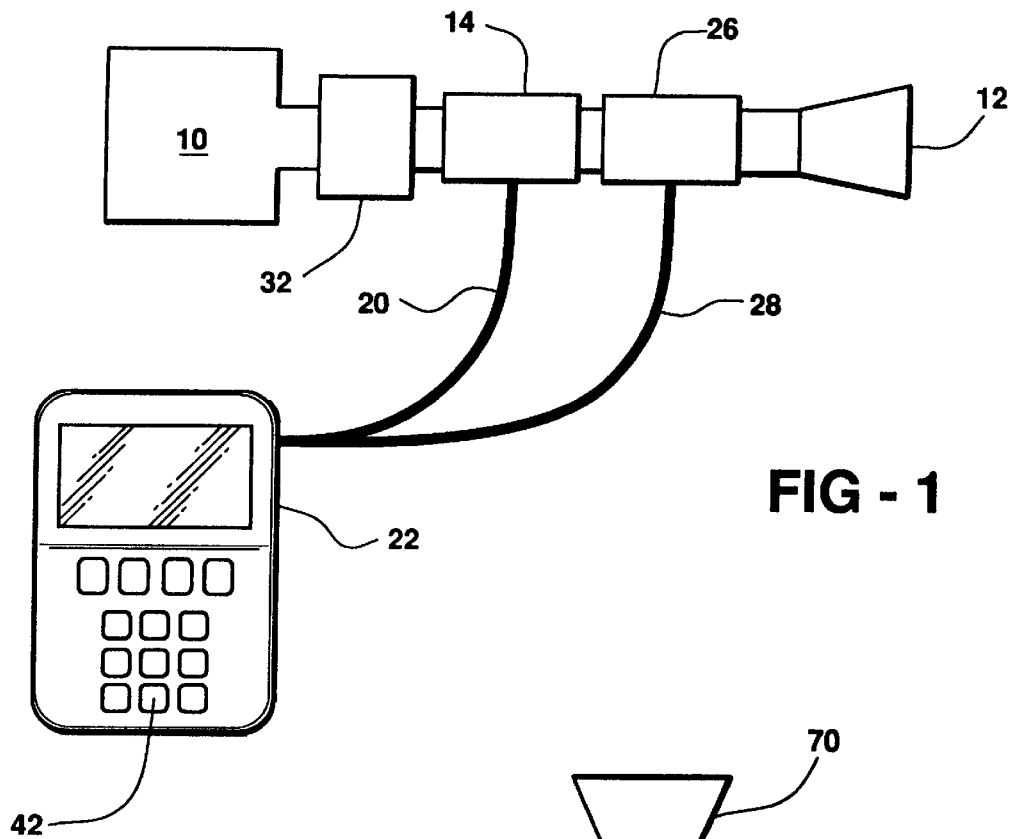
FIG. 1 is a schematic diagram of a preferred embodiment of my invention constituting a respiratory calorimeter employing a bidirectional flow and a capnometer providing electrical outputs to a microprocessor-based computer.

Referring to FIG. 1, which schematically illustrates a preferred embodiment of the present oxygen consumption meter, a source of respiratory gases, which may be ambient air or some form of positive-pressure ventilator is schematically illustrated at 10. A subject or patient whose respiratory function is being measured breathes through a respiratory connector taking the form of a mouthpiece 12 adapted to engage the inner surfaces of the user's mouth so as to form the sole passage for inhaled and exhaled air passing through the mouth. A nose clamp (not shown) of conventional construction may be employed to assure that all the respiratory air passes through the mouthpiece 12. In alternative configurations a mask that engages the nose as well as the mouth might be employed.

The system employs a bidirectional flow meter 14, preferably of the pressure differential type such as manufactured by Medical Graphics Corporation of St. Paul, Minnesota under the trademark "MEDGRAPHICS". Alternatively, other forms of flow transducers might be used such as a differential temperature type. The flow meter 14 is designed to accurately measure gases flowing from the device in either direction. The flow meter provides two separate tubular lines 20 to a pair of pressure transducers disposed within a microprocessor-based computation and display unit 22.

One end of the flow meter 14 is connected to a capnometer 26. The capnometer is operative to generate an electrical signal which is a function of the percentage of $CO_2$ concentration in the gas volume which it passes. The capnometer may be of a conventional type such as those described in U.S. Pat. Nos. 4,859,858; 4,859,859; 4,914,720; or 4,958,075. The electrical signal from the capnometer is provided to the microprocessor-based computer 22 over line 28.

Novametrix Medical Systems Inc. of Wallingford, Conn. manufactures a respiratory profile monitor employing a combined capnometer and flow sensor which could be used with the present invention. The other end of flow meter 14 is connected to a temperature and/or humidity conditioner unit 32. This unit acts to operate upon inhaled respiratory gases to bring either or both their moisture content or temperature into close alignment with the exhaled gases to improve the accuracy of the flow measurement made by the meter 14. The humidity conditioning function may be provided by a moisture absorbing filter such as a filter formed of fiber cellular material or a sponge, of the type termed a "artificial nose". This unit acts to absorb water vapor from gases passing through it if the water vapor content of the gases is higher than the level of moisture contained in the filter or to add water vapor to the gases if the filter vapor level is higher than that of the gases. Since the unit 32 passes both the inhaled gases and the exhaled gases, it tends to equalize them. The unit might also incorporate an active heating element to bring cooler gases from the respiratory source up to the body temperature of the exhalations.

Alternatively, the system could receive signals representing barometric pressure, room temperature, and humidity from sensors or keyboard entries and calculate correction factors for the flow measurement based on these signals. The distinction between inhalations and exhalations may be determined by the presence or absence of $CO_2$ in the flowing gas is measured by the capnometer alone or in combination with analysis of the flow meter signal by a zero crossing algorithm.

The other end of the conditioner unit 32 is connected to the respiratory gas source 10. Accordingly, upon the subject inhaling, gas is drawn through the chain of the temperature/humidity compensator 32, the capnometer 26 and the flow meter 14 from the source of respiratory gases 10. Exhalations pass through the chain of elements 32, 26 and 14 in the reverse direction.

The microprocessor-based computation and display unit 22 receives the two pressure signals from the flow meter via line 20 and from the capnometer via line 28. During a test, typically lasting 3–5 minutes, the microprocessor-based computer 22 integrates the signals from the flow meter 14 during inhalations and similarly integrates the flow meter readings during exhalations. The unit 22 may also generate a signal representative of the total volume of $CO_2$ exhaled during the test period by multiplying the percentage $CO_2$ signal on line 28 with the volume signal on line 20 and integrating the value over the test. The computer 22 can then calculate and display the oxygen consumption per unit time $VO_2$ by subtracting the exhaled $CO_2$ volume from the total exhaled volume and subtracting their difference from the inhaled volume. It can also display the exhaled $CO_2$ volume. The unit 22 preferably operates on a digital basis and if the signals on lines 20 and 28 are analog signals, as they are in the preferred embodiment of the invention, it digitizes those signals. A keyboard 42 associated with the computer 22 allows the storage and display of various factors in the same manner as the systems of my previous patents.

In addition to calculating the oxygen consumption of the subject, $VO_2$, and the resting energy expenditure in kilocalories per unit time, the computer 22 preferably generates a display of the exhaled $CO_2$ volume per unit time, RQ, which equals $VCO_2/VO_2$ and REE preferably calculated from the Weir equation: REE(KC/24 hours)=1440($VO_2 \times 3.341$)+($VCO_2 \times 1.11$) where $VO_2$ and $VCO_2$ are both measured in milliliters per minute.

Figure 2:
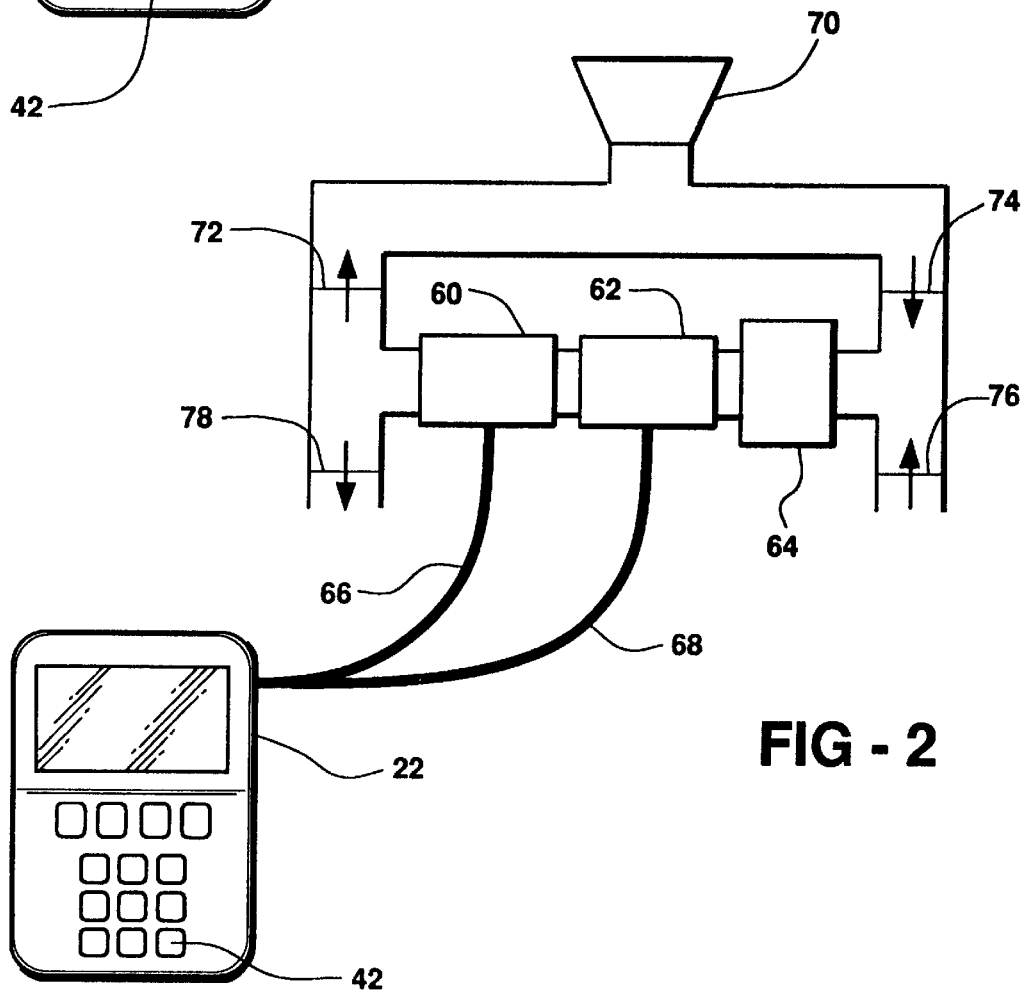
FIG. 2 is a schematic diagram of a respiratory calorimeter representing an alternative embodiment of the invention utilizing a unidirectional flow meter and conduits and valvings which direct the subject's inhalations and exhalations through the flow meter in the same direction.

An alternative embodiment of the calorimeter, illustrated in FIG. 2, employs a unidirectional flow meter 60 connected by conduits between a capnometer sensor 62 and a temperature and/or humidity conditioner 64. The flow meter 60 provides a pair of pressure signals on line 66 to appropriate transducers disposed within a microprocessor-based computer 22 having a keyboard 42 and a display. The capnometer 62 provides an electrical output signal on line 68 to the computer 22. A patient connection such as a mouthpiece 70 receives inhaled gas from the output of the flow meter 60 via a one-way valve 72. Exhalations through the mouthpiece 70 are passed by a one-way valve 74 to the inlet of the conditioner 64. The respiratory gas inlet to the device, from the ambient air or a ventilator, is through a one-way valve 76, and the outlet of the device back to that source is through a fourth one-way valve 78.

Upon the subject inhaling through the connector 70, respiratory gases are drawn in through the valve 76, pass through the series chain of the conditioner 64, capnometer 62 and flow meter 60, and are directed by the valve 72 to the mouthpiece 70. Upon exhalation the valve 72 blocks flow so that gases pass through the valve 74, through the chain 64, 62, and 60 in the same direction as the inhalation, and through the valve 78 to the source of respiratory gases since the exhalation pressure on the outlet side of valve 72 prevents flow in that direction.

In both of these embodiments it should be understood that the use of temperature and/or humidity conditioning is optional and if used is intended to improve the precision of the measurements.

Figure 3:
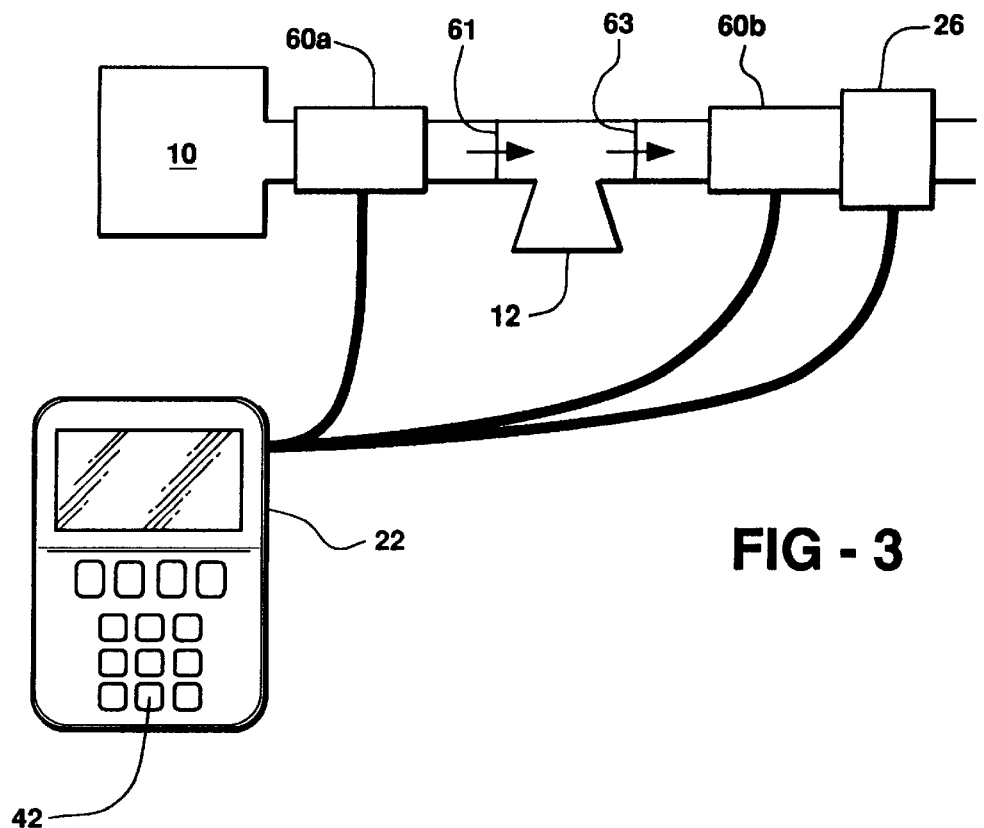
FIG. 3 is an embodiment of the indirect calorimeter employing two unidirectional flow meters.

Another embodiment of the invention, illustrated in FIG. 3, employs two unidirectional flow meters 60a and 60b, both connected to a computer 22. The outlet of flow meter 60a is connected to the mouthpiece 12 through a one-way valve 61 and the output of the mouthpiece 12 is connected to the inlet of the second flow meter 60b via a second one-way valve 63. The output of flow meter 60b passes through a capnometer 26 to the source 10. The capnometer is also connected to the computer.

This embodiment is simple and provides the accuracy of unidirectional flow meters.

Figure 4:
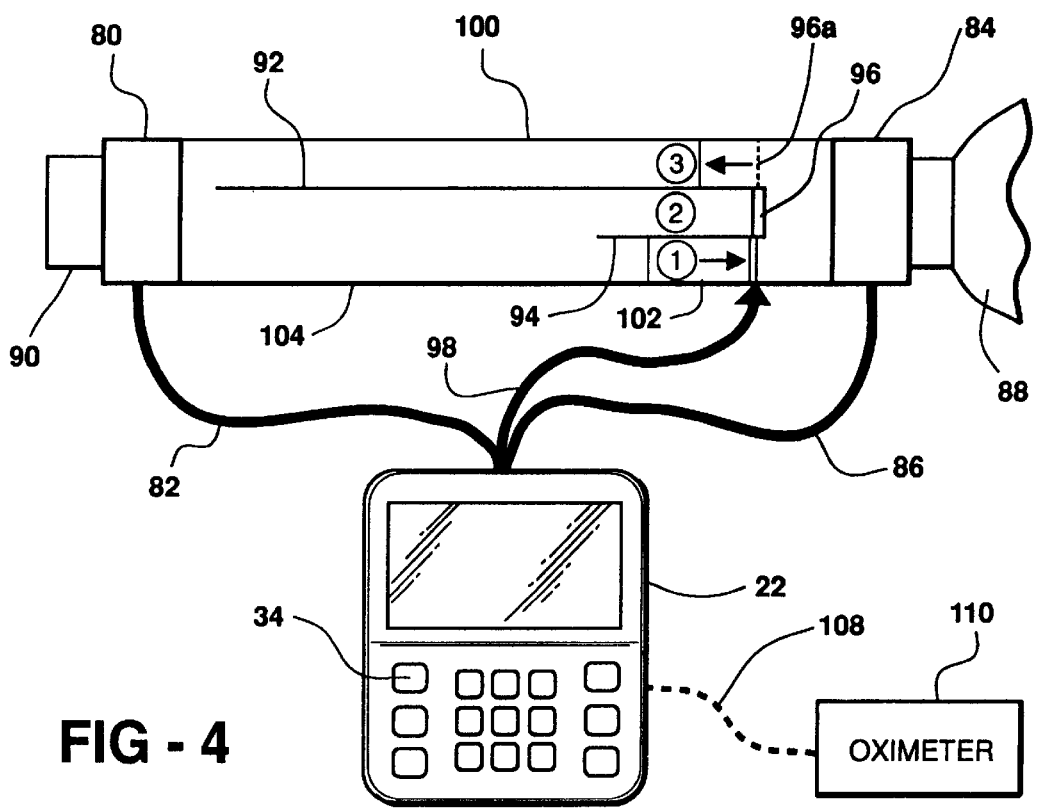
FIG. 4 is a schematic diagram of another embodiment of the invention constituting an oxygen consumption system and cardiac output measurement system.

An alternative embodiment of the invention illustrated in FIG. 4 allows the measurement of the subject's Cardiac Output (CO) as well as oxygen consumption and the other parameters measured by the previous embodiments of the invention. Like the embodiment of FIG. 1, the system of FIG. 4 employs a bidirectional volume flow meter 80 operative to provide pressure signals as a function of the instantaneous gas flow volume through it on line 82 to transducers forming part of a microprocessor-based computer and display unit 22 having an input keyboard 34. It also employs a capnometer sensor 84 which provides an electrical output representative of the instantaneous percentage of $CO_2$ in the gas passing through the capnometer, on line 86 to the microprocessor based computer 22.

One side of the capnometer is connected to a respiratory connector mouthpiece 88. One side of the bidirectional volume flow meter 80 is connected to a source of respiratory gases 90 which is preferably ambient air. The unit could incorporate humidity and/or temperature sensors like the other embodiments or the microprocessor could make calculations based on ambient temperature, barometric pressure and humidity to compensate the flow sensor readings.

The passageways interconnecting the flow meter 80 and the capnometer 84 include a partition wall 92 extending from near one end of the flow meter 80 to near one end of capnometer sensor 84. A shorter partition 94 extends parallel to the partition 92 adjacent the capnometer sensor. A switchable partition 96 may be controlled by a signal on line 98 from the microprocessor 22 to move between the illustrated position in which it extends between the two ends of the partitions 92 and 94 and blocks flow between them, and an alternative position, illustrated in phantom lines as 96a where it unblocks the space between the partitions 92 and 94 and instead blocks the space between one end of the partition 92 and wall 100 of the conduit interconnecting the flow meter 80 and the capnometer 84.

To make a measurement of oxygen consumption, the partition 96 is switched to the position illustrated in FIG. 4 in which it extends between the ends of the partitions 92 and 94 and blocks the passage of gases between them. When the subject inhales through the mouthpiece 88, respiratory gases are drawn from the source 90 through the bidirectional flow meter 80 and through a one-way valve 102 which extends between the partition 94 and the conduit wall 104. Exhalations through the mouthpiece 88 pass through the capnometer 84 and then through a one-way valve 106 which extends between the end of the partition 92 near the capnometer and the wall 100 of the conduit. Then the exhalations pass out the bidirectional flow meter 80 to the source of respiratory gases 90.

Like the embodiments of FIGS. 1 and 2, the computer 22, receiving signals from the flow sensor and the capnometer, generates the signal $VO_2$ by subtracting the exhalation flow volume, less the volume of $CO_2$ in the exhalation, as calculated by integrating the instantaneous $CO_2$ signal from the capnometer 84 over the exhalation flow signal from the flow sensor 80, from the inhalation volume as measured by the flow meter 80. REE and RQ may be calculated in the same manner as in the previous embodiments.

The unit may be used to calculate Cardiac Output in the same manner as the combined oxygen and cardiac output analyzer disclosed in my pending U.S. patent application filed on Mar. 11, 1997. This implements the nonevasive method of cardiac output measurement using $CO_2$ rebreathing described in an article by Capek and Roy in the *IEEE Transactions in Biomedical Engineering*, Volume 35, pages 653–61, 1988. Essentially, with the partition 96 in the position illustrated in FIG. 4, $VO_2$, $VCO_2$, and end-tidal $CO_2$ (et$CO_2$) are recorded over 3 minutes. The occurrence of the end-tidal time is detected by examining the output of either the flow sensor or the capnometer. The partition 96 is then switched so that the input to valve 106 is blocked. During exhalation, a portion of the exhaled breath is stored in the volume between the partition 92 and the wall 104. When the user inhales, the initial portion of the inhalation constitutes this previously breathed gas and the balance is drawn from the respiratory gas source 90 through the bidirectional volume flow meter 80. During this period, the breath-to-breath et$CO_2$ and total $VCO_2$ are recorded. The computer 22 then implements the calculation:

$$C.O. = \frac{\Delta VCO_2}{\Delta etCO_2}$$

where $\Delta VCO_2$ equals the difference in the total volume of exhaled $CO_2$, per breath, during the two recordings and $\Delta etCO_2$ is the change in the end-tidal $CO_2$ content of an exhalation between the first recording and the second recording, with the end-tidal point detected by a zero crossing algorithm in the microprocessor.

FIG. 4 illustrates an alternative embodiment in which line 108 provides the output signal from a continuous pulse oximeter 110, preferably of the type attached to a subject's finger, to allow the measurement of Delivered Oxygen ($DO_2$). The measured or estimated hemoglobin value of the subject is entered via keyboard 24 by the operator. The computer then implements the equation:

$$DO_2 = (C.O.)(SpO_2)(Hgb)(1.36)$$

where $SpO_2$ equals the blood oxygenation as measured by the oximeter 110.

Having thus disclosed my invention, I claim:

1. An indirect calorimeter operative to measure the respiratory oxygen consumption per unit time of a subject, comprising:
   a respiratory connector operative to be supported in contact with a subject so as to pass respiratory gases as the subject breathes into said respiratory connector;
   a flow meter operative to generate signals as a function of the volume of gases passed through the flow meter;

a capnometer operative to generate signals as a function of the instantaneous carbon dioxide content of gases passed through the capnometer;

an electronic computer operative to receive signals from the flow meter and the capnometer; and conduits interconnecting the respiratory connector, the flow meter and the capnometer so that the subject's inhalations and exhalations pass through the flow meter and the subject's exhalations pass through the capnometer; the computer being operative to receive the signals from the capnometer and the flow meter to calculate the subject's oxygen consumption over the period of the test.

2. The indirect calorimeter of claim 1 wherein the computer calculates the subject's oxygen consumption over the period of the test ($VO_2$) by implementing the equation:

$$VO_2 = V_i - (V_e - VCO_2)$$

where $V_i$ equals the inhaled volume; $V_e$ equals the exhaled volume and $VCO_2$ equals the exhaled $CO_2$ volume calculated from the instantaneous $CO_2$ measurement of the capnometer and the instantaneous output of the flow meter.

3. The indirect calorimeter of claim 1 wherein the flow meter is the unidirectional type and the calorimeter includes directional valves interconnected with the conduits to cause both the inhalations and the exhalations to pass through the flow meter in the same direction.

4. The indirect calorimeter of claim 1 wherein the flow meter is bidirectional.

5. The indirect calorimeter of claim 1 wherein the flow meter comprises two unidirectional flow meters interconnected so that the subject's inhalations pass through one flow meter and the subject's exhalations pass through the other flow meter.

6. The indirect calorimeter of claim 1 further including temperature conditioning means connected in said conduits so as to alter the temperature of respiratory gases flowing through it to generally equalize the temperature of the inhalations and exhalations passing through the flow meter.

7. The indirect calorimeter of claim 1 further including humidity conditioning means connected in said conduits so as to pass respiratory gases to generally equalize the humidity of the inhalations and exhalations passed through the flow meter.

8. The indirect calorimeter of claim 1 further including a source of respiratory gases and switch means moveable between a first position wherein an inhalation draws through the respiratory connector gases which are substantially from said source of respiratory gases, and a second position wherein an inhalation provides to the respiratory connector an initial quantity of gases representing the gases expired during the previous exhalation and the balance of the gases during said inhalation constitute gases from said respiratory connector, and wherein said means for receiving the signals from the flow meter and the capnometer operate to compute the subject's Cardiac Output based upon signals generated while said switch means was initially in said first position and then subsequently in said second position.

9. The indirect calorimeter of claim 8 wherein said means for receiving signals from the flow sensor and the capnometer calculates and stores, while said switch means is in the first position, the subject's oxygen consumption, $CO_2$ expiration and the end-tidal $CO_2$ and while the switch is in the second position calculates the end-tidal $CO_2$ and total expired $CO_2$ and calculates Cardiac Output by the equation:

$$C.O. = \frac{\Delta VCO_2}{\Delta etCO_2}$$

where $\Delta VCO_2$ equals the difference in the total volume of exhaled $CO_2$, per breath, during the two periods and $\Delta etCO_2$ constitutes the difference in the end-tidal $CO_2$, per breath, during the two periods.

10. The indirect calorimeter of claim 9 wherein the end-tidal $CO_2$ content of an exhalation is detected using a zero crossing algorithm.

11. An indirect calorimeter operative to measure the respiratory oxygen consumption per unit time of a subject, comprising:

a source of respiratory gases;

a respiratory connector operative to be supported in contact with the subject so as to pass respiratory gases as the subject breathes into said respiratory connector;

a flow meter operative to generate signals as a function of the volume of the gases passed through the flow meter;

a capnometer operative to generate a signal as a function of the instantaneous $CO_2$ content of the gases passed through the capnometer;

conduits interconnecting said source of respiratory gases, said respiratory connector, flow meter and capnometer operative, upon the subject inhaling, to cause respiratory gas from said source to pass through said flow meter to the respiratory connection, and upon the subject exhaling to pass the exhaled gas through the capnometer and the flow meter, and means for receiving the resultant signals from the flow meter and the capnometer and for calculating the volume of $CO_2$ exhaled by the subject over a period of time as the integral of the instantaneous flow meter signals multiplied by the capnometer signals over that period and for calculating the oxygen consumption over the period by subtracting the volume of exhaled respiratory gases over the period less the calculated volume of $CO_2$ expired over the period from the volume of gases inhaled during the period.

12. The indirect calorimeter of claim 11 in which the flow meter means is unidirectional and further including valves interconnected in the conduits to cause both the inhaled and exhaled gases to pass through the flow meter in the same direction.

13. The indirect calorimeter of claim 11 in which the flow meter means comprises two unidirectional flow meters, one connected to pass the subject's inhalations and the other to pass the subject's exhalations.

14. The indirect calorimeter of clam 12 where the valve means comprises four one-way valves, a first connected between the source of respiratory gases and inlet to the flow meter to allow gases from the respiratory source to pass through the flow meter from the respiratory source, a second connected in conduits extending from the output of the respiratory source to the respiratory connector to allow inhaled gases from the respiratory source to pass to the respiratory connector after passing through the flow meter, a third in a conduit extending from said respiratory connector to the inlet of the flow meter operative to allow gases exhaled through the respiratory connector to pass through the flow meter, and a fourth disposed in a conduit extending from the output of said flow meter to said source of respiratory gases to allow exhaled gases from the flow meter to return to the source of respiratory gases.

15. The method of measuring the respiratory oxygen consumption of a subject per unit time, comprising measuring the volume of respiratory gases inhaled and exhaled by the subject over a period of time using a flow meter and the volume of carbon dioxide in the exhaled gas as computed by integrating over the measurement period the instantaneous carbon dioxide percentage of the exhaled gas as measured by a capnometer, multiplied by the volume of exhaled gases passing through the flow meter at the same time, and implementing the calculation $VO_2=V_i-(V_e-VCO_2)$ where $VO_2$ equals the oxygen consumption; $V_i$ equals the inhaled volume; $V_e$ equals the exhaled volume and $VCO_2$ equals the exhaled $CO_2$.

16. The method of claim 15 further comprising modifying the temperature of the inhaled gases during the measurement period, before passing the inhaled gases through the flow meter, to substantially equate the temperature of the inhaled and exhaled gases.

17. The method of claim 15 further comprising calculating the subject's Cardiac Output by measuring the end-tidal $CO_2$ based on the output of the capnometer at points in time determined by a zero crossing algorithm applied to the output of the flow meter and configuring connections between the source of respiratory gases, the flow meter and the respiratory connector so that during a first period of time, inhaled gases applied to the respiratory connector are drawn essentially from the source of respiratory gases and during a second period of time gases applied to the respiratory connector during an inhalation initially constitute previously exhaled gases, with the balance of the inhalation comprising gases from the source of respiratory gases and performing the computation $$C.O. = \frac{\Delta VCO_2}{\Delta etCO_2}$$

where $\Delta VCO_2$ equals the difference in the total volume of exhaled $CO_2$, per breath, during the time that the system is in the two configurations and $\Delta etCO_2$ constitutes the difference in end-tidal $CO_2$ as measured while the system is in the two configurations.

18. The method of claim 15 further comprising measuring the subject's Delivered Oxygen ($DO_2$) by measuring the subject's blood oxygenation ($SpO_2$), measuring or estimating the subject's hemoglobin (Hgb) and implementing the equation:

$$DO_2=(C.O.)(SpO_2)(Hgb)(1.36).$$

* * * * *